US010919819B2

(12) United States Patent
Sujith et al.

(10) Patent No.: US 10,919,819 B2
(45) Date of Patent: Feb. 16, 2021

(54) OLIGOMERIZATION OF ETHYLENE

(71) Applicants: SK Innovation Co., Ltd., Seoul (KR); SK Global Chemical Co., Ltd., Seoul (KR)

(72) Inventors: Sudevan Sujith, Daejeon (KR); So Hee Sim, Daejeon (KR); Hyo Seung Park, Daejeon (KR); Sun Young Kim, Daejeon (KR); Sang Ick Lee, Daejeon (KR); Han Sol Lee, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 16/317,579

(22) PCT Filed: Jul. 5, 2017

(86) PCT No.: PCT/KR2017/007143
§ 371 (c)(1),
(2) Date: Jan. 14, 2019

(87) PCT Pub. No.: WO2018/012792
PCT Pub. Date: Jan. 18, 2018

(65) Prior Publication Data
US 2019/0284109 A1 Sep. 19, 2019

(30) Foreign Application Priority Data

Jul. 14, 2016 (KR) .................. 10-2016-0089159
May 19, 2017 (KR) .................. 10-2017-0062436

(51) Int. Cl.
C07C 2/36 (2006.01)
B01J 31/14 (2006.01)
B01J 31/24 (2006.01)
C08F 10/02 (2006.01)
C08F 4/69 (2006.01)
C07C 2/08 (2006.01)
C07F 9/28 (2006.01)
C08F 2/06 (2006.01)
C07C 2/32 (2006.01)
C07C 2/24 (2006.01)

(52) U.S. Cl.
CPC .............. C07C 2/36 (2013.01); B01J 31/143 (2013.01); B01J 31/2409 (2013.01); C07C 2/08 (2013.01); C07F 9/28 (2013.01); C08F 4/69086 (2013.01); C08F 10/02 (2013.01); B01J 2231/20 (2013.01); B01J 2531/007 (2013.01); B01J 2531/62 (2013.01); C07C 2/24 (2013.01); C07C 2/32 (2013.01); C07C 2531/14 (2013.01); C07C 2531/24 (2013.01); C08F 2/06 (2013.01); Y02P 20/52 (2015.11)

(58) Field of Classification Search
CPC .... C07C 2/36; C07C 2/08; C07C 2/32; C07C 2/24; C07C 2531/14; C07C 2531/24; C07F 9/28; C08F 4/69086; C08F 10/02; C08F 2/06; B01J 31/143; B01J 31/2409; B01J 2231/20; B01J 2531/007; B01J 2531/62; B01J 31/128; Y02P 20/52
See application file for complete search history.

(56) References Cited

U.S. PATENT DOCUMENTS

| | | | |
|---|---|---|---|
| 3,906,053 A | 9/1975 | Lanier | |
| 6,184,428 B1 | 2/2001 | Zahoor et al. | |
| 6,800,702 B2 | 10/2004 | Wass | |
| 7,511,183 B2 | 3/2009 | Blann et al. | |
| 7,994,363 B2 | 8/2011 | Gao et al. | |
| 8,309,779 B2 | 11/2012 | Han et al. | |
| 8,367,786 B2 † | 2/2013 | Dixon | |
| 8,609,924 B2 | 12/2013 | Han et al. | |
| 9,266,983 B2 | 2/2016 | Li et al. | |
| 9,688,588 B2 | 6/2017 | Zoricak et al. | |
| 2005/0113622 A1* | 5/2005 | Drent | C07C 2/36 585/521 |
| 2008/0058486 A1* | 3/2008 | McCullough | C07C 2/36 526/161 |
| 2010/0137669 A1* | 6/2010 | Han | C07C 2/34 585/514 |
| 2010/0145124 A1* | 6/2010 | Han | C07C 2/36 585/528 |
| 2010/0240847 A1* | 9/2010 | Dixon | C07C 2/36 526/161 |
| 2012/0130086 A1* | 5/2012 | Han | C07C 2/36 548/402 |

(Continued)

FOREIGN PATENT DOCUMENTS

KR 20030046401 A 6/2003
KR 1020080068226 A 7/2008

(Continued)

OTHER PUBLICATIONS

Wang et al., "Mixed aluminoxanes: efficient cocatalysts for bisphosphineamine/Cr(III) catalyzed ethylene tetramerization toward 1-octene", Applied Petrochemical Research, 2015, pp. 143-149, vol. 5, Issue 2.

Primary Examiner — Ali Z Fadhel
(74) Attorney, Agent, or Firm — The Webb Law Firm

(57) ABSTRACT

Provided is a method for oligomerization of ethylene, and more particularly, a method for producing 1-hexene and 1-octene at a high selectivity under an ethylene atmosphere by inducing a remarkably improved catalytic activity while effectively reducing a production amount of polyethylene by introducing the oligomerization catalyst and a cocatalyst mixture containing at least two aluminums together and adjusting the kind of oligomerization catalyst and injection conditions thereof.

13 Claims, No Drawings

(56) References Cited

U.S. PATENT DOCUMENTS

| | | | | |
|---|---|---|---|---|
| 2014/0142360 A1* | 5/2014 | Brown | ................... | C07C 2/36 |
| | | | | 585/512 |
| 2015/0045603 A1* | 2/2015 | Han | ................... | B01J 31/143 |
| | | | | 585/511 |
| 2016/0303551 A1* | 10/2016 | Zoricak | ............... | B01J 31/143 |

FOREIGN PATENT DOCUMENTS

| | | | |
|---|---|---|---|
| KR | 1020090017929 A | | 2/2009 |
| KR | 1020100087913 A | | 8/2010 |
| KR | 101065596 B1 | | 9/2011 |
| KR | 1020140066562 A | | 6/2014 |
| KR | 1020140124732 A | | 10/2014 |
| RU | 2556636 C1 | | 7/2015 |
| RU | 2581052 C1 | | 4/2016 |
| WO | 0204119 A1 | | 1/2002 |
| WO | 2004056478 A1 | | 7/2004 |
| WO | 2014094114 A1 | | 6/2014 |
| WO | 2015/097599 A1 | † | 7/2015 |

\* cited by examiner
† cited by third party

OLIGOMERIZATION OF ETHYLENE

CROSS-REFERENCE TO RELATED APPLICATIONS

This application is the United States national phase of International Application No. PCT/KR2017/007143 filed Jul. 5, 2017, and claims priority to Korean Patent Application Nos. 10-2016-0089159 and 10-2017-0062436 filed Jul. 14, 2016 and May 19, 2017, respectively, the disclosures of which are hereby incorporated in their entirety by reference.

TECHNICAL FIELD

The present invention relates to a method for oligomerization of ethylene, and more specifically, to a method for trimerization and/or tetramerization of ethylene.

BACKGROUND ART

Linear alpha-olefins (LAO) play very important roles as a reaction intermediate used for a comonomer, a detergent, a lubricant, and a plasticizer, etc. In particular, 1-hexene and 1-octene are used as comonomers for adjusting density by forming branches in a polymer backbone at the time of producing linear low-density polyethylene (LLDPE).

The linear alpha-olefins necessary for the production of such high value-added linear low-density polyethylene are obtained by an oligomerization reaction of olefins. However, the oligomerization reaction of olefins produce a considerable amount of butene, other olefins and isomers thereof, specific higher oligomers, polymers (polyethylene), etc., together, which is unwanted.

As conventional techniques of oligomerization of olefins, Prior art document 1 discloses an oligomerization technology of ethylene using a nickel-based catalyst including 2-diphenylphosphino benzoic acid (DPPBA) as a chelate ligand, $NiCl_2$ as a nickel precursor, $6H_2O$, sodium tetraphenylborate as a catalytic activator, which is known to produce 1-octene with selectivity of 19%. Further, Prior art document 2 discloses a Ziegler-type catalyst based on a trialkylaluminum catalyst, which is known to produce about 13 to 25 mass % of 1-octene with respect to an olefin mixture.

Further, studies on the production of 1-hexene and 1-octene by selective oligomerization of ethylene through transition metal catalysts have been conducted, and most of these known transition metal catalysts are chromium-based catalysts. Related art documents associated with this are Prior art documents 3 to 8.

However, in spite of the fact that the related art documents using the chromium-based catalyst have a number of advantages, there is still a need for a technique capable of producing trimerization and tetramerization with high activity and selectivity while simultaneously suppressing production of polyolefins to perform a stable operation.

Related Art Document (Prior art document 1) U.S. Pat. No. 6,184,428
(Prior art document 2) U.S. Pat. No. 3,906,053
(Prior art document 3) International Patent No. WO 2002-004119
(Prior art document 4) International Patent No. WO 2004-056478
(Prior art document 5) U.S. Pat. No. 7,994,363
(Prior art document 6) Korean Patent Laid-Open Publication No. 10-2008-0068226
(Prior art document 7) Korean Patent Laid-Open Publication No. 10-2009-0017929
(Prior art document 8) Korean Patent Laid-Open Publication No. 10-2010-0087913

DISCLOSURE OF INVENTION

Technical Problem

An object of the present invention is to provide a method for oligomerization of ethylene with high catalytic activity and selectivity, particularly, a method for highly selectively producing 1-hexene and 1-octene by inhibiting formation of by-product.

Solution to Problem

In one general aspect, a method for oligomerization of ethylene includes: mixing an aluminoxane and an alkyl aluminum compound to prepare a cocatalyst mixture; introducing the cocatalyst mixture and a oligomerization catalyst including a transition metal and having a complex form, respectively, into a reactor, or mixing the cocatalyst mixture and the oligomerization catalyst and introducing a mixture of the cocatalyst mixture and the oligomerization catalyst into the reactor; introducing ethylene into the reactor; and reacting the oligomerization catalyst, the cocatalyst mixture, and the ethylene in the reactor with each other.

The aluminoxane may be methylaluminoxane or modified methylaluminoxane, and the alkyl aluminum compound may be one or more selected from isobutylaluminoxane, tetraisobutylaluminoxane, trimethylaluminum, triethylaluminum, tripropylaluminum, triisobutylaluminum, diisobutylaluminum, and trioctylaluminum, etc.

The oligomerization catalyst may be a complex in which the transition metal and a heteroatom ligand represented by Chemical Formula 1 below are coordinated to each other:

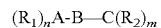  [Chemical Formula 1]

in Chemical Formula 1,

A and C are each independently selected from the group consisting of phosphorus, arsenic, antimony, oxygen, bismuth, sulfur, selenium, and nitrogen;

B is a linking group between A and C, $R_1$ and $R_2$ are each independently substituted or unsubstituted hydrocarbyl or substituted or unsubstituted heterohydrocarbyl, and n and m are each independently determined by each valence and oxidation state of A or C.

The linking group B in Chemical Formula 1 above may be selected from an organic linking group including substituted or unsubstituted hydrocarbylene and substituted or unsubstituted heterohydrocarbylene; and an inorganic linking group including a single atom link.

The heteroatom ligand may be represented by Chemical Formula 2 below:

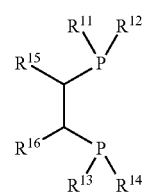  [Chemical Formula 2]

in Chemical Formula 2, $R^{11}$ to $R^{14}$ are each independently substituted or unsubstituted hydrocarbyl or substituted or unsubstituted heterohydrocarbyl; and $R^{15}$ and $R^{16}$ are each independently substituted or unsubstituted hydrocarbyl, or $R^{15}$ and $R^{16}$ may be bonded to each other to form a ring.

$R^{15}$ and $R^{16}$ in Chemical Formula 2 above may be bonded to each other to form an alicyclic ring or aromatic ring.

The transition metal may be chromium.

The cocatalyst mixture may be introduced into the reactor at a range from 1 to 10000 moles based on 1 mole of the oligomerization catalyst.

The cocatalyst mixture may include the aluminoxane and the alkyl aluminum compound at a molar ratio of 1:0.01 to 1:100.

The reaction of the oligomerization catalyst, the cocatalyst mixture, and the ethylene in the reactor with each other may be performed in the presence of hydrogen.

The reaction of the oligomerization catalyst, the cocatalyst mixture, and the ethylene in the reactor with each other may be performed at a temperature range from 0 to 200° C.

The reaction of the oligomerization catalyst, the cocatalyst mixture, and the ethylene in the reactor with each other may be performed at a temperature range from 40 to 100° C.

The reaction of the oligomerization catalyst, the cocatalyst mixture, and the ethylene in the reactor with each other may be performed at a pressure range from 1 to 500 bar.

1-hexene, 1-octene, or a mixture thereof may be selectively produced.

Advantageous Effects of Invention

According to the present invention, the activity and selectivity of the conversion of ethylene to 1-hexene and 1-octene can be easily controlled by the combination of the respective catalyst components and reactor feed conditions thereof, etc. In particular, a cocatalyst mixture containing at least two aluminum compounds may be introduced to implement rapid initiation, stable operation, and good reproducibility of the oligomerization reaction of ethylene with remarkably improved catalytic activity.

According to the present invention, high oligomerization activity can be obtained even at a low reaction temperature, and thus, it is possible to overcome technical obstacles i.e. reducing a production amount of polyethylene, and to achieve an unexpected synergistic effect, thereby providing an economical method for producing 1-hexene and 1-octene.

BEST MODE FOR CARRYING OUT THE INVENTION

Hereinafter, a method for oligomerization of ethylene according to the present invention will be described in detail. Unless technical and scientific terms used herein are defined otherwise, they have meanings understood by those skilled in the art to which the present invention pertains. In the following description, well-known functions and components which obscure the description and the accompanying drawings of the present invention with unnecessary detail will be omitted.

According to an exemplary embodiment of the present invention, in the case of a low degree of ethylene polymerization, it is possible to provide a characteristically high catalytic activity, and to prevent the decrease in catalytic activity during a reaction by effectively suppressing the formation of high molecular weight of polyethylene.

In addition, according to an exemplary embodiment of the present invention, particularly, ethylene may be trimerized and/or tetramerized to produce 1-hexene and 1-octene with high selectivity.

In the ethylene oligomerization process according to an exemplary embodiment of the present invention, a cocatalyst mixture containing at least two different aluminum compounds is used.

Specifically, the ethylene oligomerization process according to an exemplary embodiment of the present invention may include: mixing an aluminoxane and an alkyl aluminum compound to prepare a cocatalyst mixture; introducing the cocatalyst mixture and a oligomerization catalyst including a transition metal, respectively, into a reactor, or mixing the cocatalyst mixture and the oligomerization catalyst and introducing a mixture of the cocatalyst mixture and the oligomerization catalyst into the reactor; introducing ethylene into the reactor; and reacting the oligomerization catalyst, the cocatalyst mixture, and the ethylene in the reactor.

In the ethylene oligomerization process according to an exemplary embodiment of the present invention, it is preferred that the cocatalyst mixture and the oligomerization catalyst are mixed and introduced into the reactor to thereby remarkably improve a catalytic activity, and at the same time, to remarkably reduce the formation of polyethylene that inhibits process operation stability when producing linear alpha-olefin, thereby effectively preventing a sticking phenomenon by the polyethylene in the reactor. However, in an exemplary embodiment of the present invention, the cocatalyst mixture and the oligomerization catalyst may be introduced into the reactor, respectively. Here, the polyethylene is a by-product produced during the reaction which is accumulated inside the reactor causing heat transfer disturbance, thereby inhibiting a linear alpha-olefin production yield and inducing the process not to be operated for a long period of time.

In the ethylene oligomerization process according to an exemplary embodiment of the present invention, the aluminoxane may be a linear form, a cyclic form, a cage-type form, etc. Non-limiting examples thereof may be selected from alkylaluminoxane selected from methylaluminoxane (MAO), methylisobutylaluminoxane (MMAO), ethylaluminoxane (EAO), isobutylaluminoxane (IBAO), tetraisobutylaluminoxane (TIBAO), etc., and modified alkylaluminoxane (for example, $[(R^a)_n(R^b)_{1-n}AlO]_m$, wherein $R^a$ and $R^b$ are each independently hydrocarbyl, hydrocarbyl substituted with halogen, or halogen, n is between 0 and 1, and m is an integer of 1 or more) such as modified methylaluminoxane (mMAO), etc. Further, examples of commercially available modified methylaluminoxane (mMAO) may include mMAO-12, mMAO-3A, and mMAO-7, etc., but the present invention is not limited thereto.

When at least one aluminoxane is mixed with at least one alkyl aluminum compound to be used as the cocatalyst of the catalyst composition for ethylene oligomerization according to an exemplary embodiment of the present invention, it was found that formation of the polymer was decreasing remarkably, and at the same time, the catalytic activity of the oligomerization catalyst to be introduced thereafter could be remarkably improved as compared to a case where a cocatalyst containing one kind of aluminum compound was used. In particular, a combination of an aluminoxane of methylaluminoxane or modified methylaluminoxane and the alkyl aluminum compound to be described below exhibits a remarkable effect.

Here, non-limiting examples of the alkyl aluminum compound may include alkyl aluminum such as trimethyl aluminum, triethyl aluminum, tripropyl aluminum, tri-isobutyl aluminum, diisobutyl aluminum, and trioctyl aluminum, etc.; alkyl aluminum chloride such as dimethyl aluminum chloride, diethyl aluminum chloride, dipropyl aluminum chloride, diisobutyl aluminum chloride, dioctyl aluminum chloride, methyl aluminum dichloride, ethyl aluminum dichloride, propyl aluminum dichloride, isobutyl aluminum dichloride, hexyl aluminum dichloride, methyl aluminum sesquichloride, and ethyl aluminum sesquichloride, etc; dialkylaluminum hydride such as dimethylaluminum hydride, diethylaluminum hydride, dipropylaluminum hydride, diisopropylaluminum hydride, diisobutylaluminum hydride, and dioctylaluminum hydride, etc.; alkyloxy aluminum compound such as dimethyl aluminum methoxide, diethyl aluminum ethoxide, and diisobutyl aluminum isopropoxide, etc.; aryloxyaluminum such as triphenoxy aluminum, dimethyl aluminum phenoxide, and methyl aluminum diphenoxide, etc.; alkylaluminoxane such as isobutylaluminoxane (IBAO), and tetraisobutylaluminoxane (TIBAO), etc.

Preferred examples of the cocatalyst mixture of the catalyst composition for oligomerization of ethylene according to an exemplary embodiment of the present invention may be a mixture of aluminoxane from methylaluminoxane or modified methylaluminoxane with at least one alkylaluminum compound selected from isobutylaluminoxane, tetraisobutylaluminoxane, trimethylaluminum, triethylaluminum, tripropylaluminum, triisobutylaluminum, diisobutylaluminum and trioctylaluminum, etc., and more preferably, a combination of aluminoxane from methylaluminoxane or modified methylaluminoxane with at least one alkylaluminum compound selected from trimethylaluminum, triethylaluminum, tripropylaluminum, triisobutylaluminum, diisobutylaluminum, and trioctylaluminum, etc., but the present invention is not limited thereto.

According to an exemplary embodiment of the present invention, by using the cocatalyst mixture containing at least two aluminums, the ethylene oligomerization may be quickly initiated by rapidly and effectively activating the oligomerization catalyst, which is a catalyst for oligomerization of ethylene. Further, by using the combined catalyst system as described above, the production amount of the polyolefin may be effectively reduced. At this time, the combined catalyst system means the oligomerization catalyst and the cocatalyst mixture.

The ethylene oligomerization process according to an exemplary embodiment of the present invention may provide synergistic effects with the cocatalyst mixture by appropriately adjusting the kind of oligomerization catalyst and reactant feeding conditions thereof, etc.

First, according to an exemplary embodiment of the present invention, the cocatalyst mixture and the oligomerization catalyst including the transition metal and having a complex form may be introduced into the reactor, respectively, or may be mixed and introduced into the reactor.

As described above, by using the oligomerization catalyst in the form of a complex, the catalyst form may be stable to maintain a remarkably improved catalytic activity during the process, and to implement a stable operation and good reproducibility in the process.

The oligomerization catalyst of the catalyst composition for oligomerization of ethylene according to the present invention is not particularly limited as long as it is a catalyst in the form of a complex capable of oligomerizing ethylene, preferably, may have a complex form in which a transition metal and a heteroatom ligand are coordinated to each other. Here, the preferred oligomerization catalyst according to the present invention may have a complex form in which a transition metal and a heteroatom ligand represented by Chemical Formula 1 below are coordinated to each other:

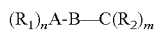  [Chemical Formula 1]

in Chemical Formula 1,

A and C are each independently selected from the group consisting of phosphorus, arsenic, antimony, oxygen, bismuth, sulfur, selenium, and nitrogen;

B is a linking group between A and C, $R_1$ and $R_2$ are each independently substituted or unsubstituted hydrocarbyl or substituted or unsubstituted heterohydrocarbyl, and n and m are each independently determined by each valence and oxidation state of A or C.

The hydrocarbyl or heterohydrocarbyl means a radical having one bonding position derived from (C1-C30)hydrocarbon or (C1-C30)heterohydrocarbon, and the hydrocarbylene or heterohydrocarbylene means a radical having two bonding positions derived from (C1-C30)hydrocarbon or (C1-C30)heterohydrocarbylene, and the hetero means substitutions in which carbons are substituted with heteroatoms such as O, S, N, B, Si, P, etc.

Further, the substitution may be each independently selected from the group consisting of (C1-C30)hydrocarbyl, (C1-C30)heterohydrocarbyl, and halogen, etc. Non-limiting examples thereof may be selected from (C6-C20)aryl, (C6-C20)ar(C1-C10)alkyl, (C1-C10)alkyl, (C2-C10)alkenyl, (C2-C10)alkynyl, (C3-C7)cycloalkyl, hetero(C5-C20)aryl, hetero(C3-C7)cycloalkyl, (C1-C10)alkoxy, (C6-C20)aryloxy, —$NR^{21}R^{22}$, fluoro, chloro, bromo, and iodo, etc., and $R^{21}$ and $R^{22}$ are each independently substituted or unsubstituted hydrocarbyl or substituted or unsubstituted heterohydrocarbyl, and follow the definition described above.

The linking group B of the heteroatom ligand according to an exemplary embodiment of the present invention may be selected from an organic linking group including substituted or unsubstituted hydrocarbylene and substituted or unsubstituted heterohydrocarbylene; and an inorganic linking group including a single atom link Non-limiting examples thereof may be selected from organic linking groups such as methylene, dimethylmethylene, ethane-1,2-diyl, ethene-1,2-diyl, 1,2-propylene, propane-1,2-diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracene-diyl, 1,2-catecholate, 1,2-diarylhydrazine-1,2-diyl(-N(Ar)—N(Ar)—, wherein Ar is an aryl group), 1,2-dialkylhydrazine-1,2-diyl (-N(Alk)-N(Alk)-, wherein Alk is an alkyl group or a cycloalkyl group), 1-alkyl-2-arylhydrazine-1,2-diyl (—N(Alk)-N(Ar)—, wherein Alk is an alkyl group or a cycloalkyl group and Ar is an aryl group), —N(R')—$X_1$—N(R")— (wherein R' and R" are independently an alkyl group, a cycloalkyl group, or an aryl group, $X_1$ is a hydrocarbylene group), =C(R')—N(R")—, =C(R')—C(R")(R''')— (wherein = represents a double bond, R', R", and R''' are independently hydrogen, an alkyl group, a cycloalkyl group or an aryl group), —B(R')—, —Si(R')$_2$—, —P(R')—, and —N(R')— (wherein R' is hydrogen, a hydrocarbyl group, a heterohydrocarbyl group or halogen), etc.; and inorganic linking groups such as a single atom, a two-atom linker spacer, etc.

Further, the preferred oligomerization catalyst according to an exemplary embodiment of the present invention may include a heteroatom ligand having a —P—C—C—P—skeleton structure, and the structure adjacent to the carbon atom between the two phosphine atoms may vary stereoscopically, and thus, the activity and selectivity of the ethylene trimerization and tetramerization can be controlled depending on the purpose.

The preferred oligomerization catalyst according to an exemplary embodiment of the present invention may be a complex in which a heteroatom ligand represented by Chemical Formula 2 below and the transition metal are coordinated to each other in view of easily controlling a space asymmetrically, and more preferably, the catalyst may include a chiral carbon having (R,R) or (S,S) arrangement pairs in the skeleton structure, but the present invention is not limited thereto:

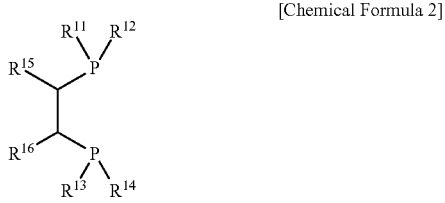

[Chemical Formula 2]

in Chemical Formula 2, $R^{11}$ to $R^{14}$ are each independently substituted or unsubstituted hydrocarbyl or substituted or unsubstituted heterohydrocarbyl; and $R^{15}$ and $R^{16}$ are each independently substituted or unsubstituted hydrocarbyl, or $R^{15}$ and $R^{16}$ may be bonded to each other via substituted or unsubstituted hydrocarbylene or substituted or unsubstituted heterohydrocarbylene to form a ring.

In the oligomerization catalyst according to an exemplary embodiment of the present invention, $R^{15}$ and $R^{16}$ in Chemical Formula 2 may be bonded to each other to form a substituted or unsubstituted alicyclic ring or a substituted or unsubstituted aromatic ring.

Further, the transition metal according to an exemplary embodiment of the present invention may also be provided by one or more chromium precursors selected from chromium (III) acetylacetonate, chromium trichloride tristetrahydrofuran, and chromium (III) 2-ethylhexanoate, etc., but the present invention is not limited thereto.

Next, according to an exemplary embodiment of the present invention, the cocatalyst mixture, and the transition metal or transition metal precursor, and the heteroatom ligand may be directly introduced into the reactor, respectively, or may be mixed and introduced into the reactor.

In the method for oligomerization of ethylene according to an exemplary embodiment of the present invention, the oligomerization catalyst may have an in situ form in which the transition metal or the transition metal precursor and the heteroatom ligand are introduced in any order. Here, the in situ form means that the transition metal or the transition metal precursor and the heteroatom ligand are directly introduced, respectively.

In the ethylene oligomerization process according to an exemplary embodiment of the present invention, the oligomerization catalyst may have an in situ form in which the transition metal or the transition metal precursor and the heteroatom ligand are introduced in any order. Here, the in situ form means that the transition metal or the transition metal precursor and the heteroatom ligand are directly introduced, respectively.

In the ethylene oligomerization process according to an exemplary embodiment of the present invention, the heteroatom ligand is not particularly limited, but when the heteroatom ligand has a —P—C—C—P-skeleton structure including phosphine atoms, it is preferred since it is possible to have a considerably stable catalytic activity, thereby preventing a decrease in a reaction rate during the reaction.

Further, in the ethylene oligomerization process of ethylene according to an exemplary embodiment of the present invention, the oligomerization catalyst having the —P—C—C—P-skeleton structure preferably includes a chiral carbon having (R,R) or (S,S) arrangement pairs in the skeleton structure. That is, the carbon atoms in the skeleton structure have four different substituents. Due to this characteristic it is possible to control the vicinity of the carbon atom to an appropriate spatial structure, thereby achieving more stable catalytic activity. It corresponds to the stabilization effect of the catalyst which is not able to be implemented in conventional oligomerization catalysts having the —P—N—P-skeleton structure known in the art.

The heteroatom ligand according to an exemplary embodiment of the present invention may be represented by Chemical Formula 2 above, and a ligand having a multiple —P—C—C—P skeleton structure may also be an exemplary embodiment of the present invention.

Specific examples of the heteroatom ligand according to an exemplary embodiment of the present invention may include (phenyl)$_2$P—CH(methyl)CH(methyl)-P(phenyl)$_2$, (4-methoxyphenyl)$_2$P—CH(methyl)CH(methyl)-P(4-methoxyphenyl)$_2$, (4-methylphenyl)$_2$P—CH(methyl)CH(methyl)-P(4-methylphenyl)$_2$, (4-ethylphenyl)$_2$ P—CH(methyl)CH(methyl)-P(phenyl)$_2$, (3-methoxyphenyl)$_2$ P—CH(methyl)CH(methyl)-P(3-methoxyphenyl)$_2$, (4-ethoxyphenyl)$_2$ P—CH(methyl)CH(methyl)-P(2-ethoxyphenyl)$_2$, (4-dimethylaminephenyl)$_2$ P—CH(methyl)CH(methyl)P(4-dimethylaminephenyl)$_2$, (4-ethylcyclohexyl)$_2$ PCH(methyl)CH(methyl)P(4-ethylcyclohexyl)$_2$, (2-ethylphenyl)$_2$ PCH(methyl)CH(methyl)P(2-ethylphenyl)$_2$, (2-isopropylphenyl)$_2$ PCH(methyl)CH(methyl)P(2-isopropylphenyl)$_2$, (2-methylphenyl)$_2$ PCH(methyl)CH(methyl)P (2-methylphenyl)$_2$, (2-ethylphenyl)$_2$ PCH(methyl)CH(methyl)P(phenyl)$_2$, (2-ethylphenyl)$_2$ PCH(ethyl)CH(methyl)P(2-ethylphenyl)$_2$, (2-ethylphenyl)$_2$ PCH(ethyl)CH(ethyl)P(2-ethylphenyl)$_2$, (2-ethylphenyl)$_2$ PCH(isopropyl) CH(methyl)P(2-ethylphenyl)$_2$, (2-ethylphenyl)$_2$ PCH(n-propyl)CH(methyl)P(2-ethylphenyl)$_2$, (2-ethylphenyl)$_2$ PCH(isopropyl)CH(ethyl)P(2-ethylphenyl)$_2$, 1,2-di-(P(2-ethylphenyl)$_2$)cyclohexane, 1,2-di-(P(2-ethylphenyl)$_2$)cyclopentane, 3,4-di-(P(2-ethylphenyl)$_2$)pyrrole, 3,4-di-(P(2-ethylphenyl)$_2$)imidazole, (2-ethylphenyl)$_2$ PCH (dimethylamine)CH(dimethylamine)P(2-ethylphenyl)$_2$, (2-methoxyphenyl)$_2$ PCH(methyl)CH(methyl)P(2-methoxyphenyl)$_2$, (2-ethoxyphenyl)$_2$ PCH(methyl)CH(methyl)P(2-ethoxyphenyl)$_2$, (2-dimethylaminephenyl)$_2$ PCH(methyl)CH(methyl)P(2-dimethylaminephenyl)$_2$, (2-ethylcyclohexyl)$_2$ PCH(methyl)CH(methyl)P(2-ethylcyclohexyl)$_2$, etc., but the present invention is not limited thereto.

In addition, the ligand of the multiple —P—C—C—P-skeleton structure is a ligand in which dendrimer ligands and individual units are combined in multiple, and non-limiting examples thereof may include 1,2,4,5-tetra-(P(2-ethylphenyl)$_2$)cyclohexane, 1,2,4,5-tetra-(P(2-ethylphenyl)$_2$)benzene, 1,2,3,4-tetra-(P(2-ethylphenyl)$_2$)cyclopentane, etc., but the present invention is not limited thereto.

In the ethylene oligomerization process of ethylene according to an exemplary embodiment of the present invention, the cocatalyst may be soluble in a solvent or may be uniformly dispersed in the solvent. Preferably, the oligomerization reaction may be performed in a C3-C20 hydrocarbon-based solvent. Here, non-limiting examples of the hydrocarbon-based solvent may include one or more selected from butane, pentane, hexane, heptane, octane, isooctane, nonane, decane, dodecane, cyclohexane, methylcyclohexane (MCH), methylcyclopentane (MCP), benzene, toluene, xylene, ethylbenzene, etc., and preferably one or more selected from cyclohexane, methylcyclohexane (MCH), methylcyclopentane (MCP), etc., but the present invention is not limited thereto.

In addition, according to an exemplary embodiment of the present invention, when the cocatalyst mixture including at least one aluminoxane and at least one alkylaluminum compound is introduced, the oligomerization of ethylene may be promoted by further including an organic boron compound.

Here, the organic boron compound is not limited as long as it is used in the art. Non-limiting examples thereof may be preferably selected from tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis(pentafluorophenyl)borate, tetrakis(2,3,5,6-tetrafluorophenyl)borate, tetrakis(2,3,4,5-tetrafluorophenyl)borate, tetrakis(3,4,5-tetrafluorophenyl)borate, tetrakis(2,2,4-trifluorophenyl)borate, phenylbis(pentafluorophenyl)borate, and tetrakis(3,5-bistrifluoromethylphenyl)borate, etc.; ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bis-trifluoromethylphenyl)borate, triethylammonium tetrakis(pentafluorophenyl)borate, tripropylammonium tetrakis(pentafluorophenyl)borate, tri(N-butyl)ammonium tetrakis(pentafluorophenyl)borate, tri(N-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, and tri(dimethylphenyl)phosphonium tetrakis(pentafluorophenyl)borate, etc. Among them, N,N-dimethylanilinium tetrakis(pentafluorophenyl)borate, triphenylmethylinium tetrakis(pentafluorophenyl)borate, and trispentafluoroborane, etc., are the most preferred, but the present invention is not limited thereto.

In the method for oligomerization according to an exemplary embodiment of the present invention, 1-butene, 1-hexene, 1-octene, 1-decene, 1-dodecene, 1-tetradecene, 1-octadecene, etc., may be produced by oligomerization of ethylene, but in particular, 1-hexene and 1-octene may be highly selectively produced. Further, according to the present invention, it was found that in the oligomerization reaction with ethylene, a production amount of polyethylene that may be formed as a by-product other than 1-hexene and 1-octene could be minimized with reduced selectivity.

Further, the oligomerization reaction may be performed in a slurry phase condition or solution phase condition, etc., and may be performed at any appropriate temperature. Here, the appropriate temperature may be from 0 to 200° C., preferably from room temperature (20° C.) to 100° C., more preferably from 40 to 70° C., which is preferred to implement high catalytic activity and high selectivity for a product. In addition, the solvent used in the solution phase condition is not limited, but may be selected from C3-C20 hydrocarbon-based solvents. Non-limiting examples of the hydrocarbon-based solvent may include one or more selected from butane, pentane, hexane, heptane, octane, isooctane, nonane, decane, dodecane, cyclohexane, methylcyclohexane (MCH), methylcyclopentane (MCP), benzene, toluene, xylene, ethylbenzene, etc., preferably, one or more selected from hexane, heptane, cyclohexane, methylcyclohexane (MCH), methylcyclopentane (MCP), etc.

Further, the oligomerization reaction according to an exemplary embodiment of the present invention may be performed at atmospheric pressure (1 bar) to 500 bar, preferably at atmospheric pressure to 100 bar, more preferably at atmospheric pressure to 60 bar, which is preferred to implement optimum catalytic activity.

In the oligomerization reaction according to an exemplary embodiment of the present invention, it was confirmed that when the reaction is performed in the presence of hydrogen, an effect of reducing the production amount of the polyethylene formed as the by-product could be maximized. That is, according to the present invention, it is possible to prevent the polymer from sticking to a reactor wall during the oligomerization reaction by significantly reducing the production amount of the polymer formed as the by-product.

In the oligomerization reaction of ethylene according to an exemplary embodiment of the present invention, the catalyst composition for oligomerization of ethylene may include the cocatalyst mixture at a range from 1 to 10000 moles based on 1 mole of the oligomerization catalyst. Preferably, the catalyst composition may be a mixture of the oligomerization catalyst and the cocatalyst mixture at a molar ratio from 1:10 to 1:10000, but the present invention is not limited thereto.

More preferably, the cocatalyst mixture in the catalyst composition mixed at the above-described range is a mixture of aluminoxane and at least one alkyl aluminum compound, and the alkyl aluminum compound may be mixed and used in a range from 0.01 to 100 moles based on the aluminoxane (1 mole) as a reference, and preferably, mixed and used in a range from 0.02 to 10 mol, and more preferably in a range from 0.1 to 5 mol, but the present invention is not limited thereto.

The present invention may be more clearly understood by Examples below, and the following examples are only provided for illustrative purposes of the present invention and are not intended to limit the scope of the invention. Further, the following Examples of the present invention were performed in a semi-batch reactor except where otherwise noted, and all of the organic solvents used in the reactions were used after passing through a tube filled with silica gel, a molecular sieve 5 A activated alumina, and bubbling with high purity nitrogen to sufficiently remove moisture, oxygen and other catalyst poison substances, etc. All reactions were performed in a nitrogen atmosphere, and most of the reagents were purchased from Aldrich or STREM. Methylaluminoxane (MAO) or modified methylaluminoxane (mMAO-3A) was purchased from AkzoNobel. A molecular weight of the methylaluminoxane was calculated as 58.016 g/mol, and a molecular weight of the modified methylaluminoxane (mMAO-3A) used in the Examples was calculated as 70.07 g/mol. The amounts of the reaction products obtained in the Examples and the Comparative Examples below were analyzed by the following methods.

[Analysis of Content (wt %) of 1-Hexene and 1-Octene in the Reaction Product (LAO)]

The reaction was completed, and then, the reaction product was filtered and separated. The separated organic layer was sampled, passed through anhydrous magnesium sulfate, and dried. Then, weight percentages (wt %) of 1-hexene and 1-octene in the reaction solution based on the total amount of MCH added to the reaction were analyzed, using Agilent GC 7890.

[Analysis of Content (wt %) of Polyethylene (PE) Obtained as a by-Product after the Reaction]

The content of polyethylene obtained as the by-product after the reaction means a content of total polyethylene including suspended polyethylene and sticking polyethylene. The floating polyethylene is a solid separated after the reaction product is filtered, and the sticking polyethylene means a solid adhered in the reactor. Each solid was dissolved in benzene heated to 70° C., and dried in a vacuum oven at 60° C. for 8 hours to remove the solvent, and weighed. Then, the weight percentage (wt %) of polyethylene was analyzed.

Synthesis Example 1

Synthesis of bis-[(S,S)-(phenyl)$_2$PCH(methyl)CH(methyl)P(phenyl)$_2$dichloride(μ-chloride)chromium] ([CrCl$_2$(μ-Cl)(P,P)-k2-(S,S)—((Ph)$_2$P(Me)CH—CH(Me)P(Ph)$_2$)]$_2$)

1.1 g (3.0 mmol) of tris(tetrahydrofuran)chromium trichloride (CrCl$_3$(THF)$_3$) was dissolved in 100 mL of dichloromethane, and 1.28 g (3.0 mmol) of (S,S)-(phenyl)$_2$PCH(methyl)CH(methyl)P(phenyl)$_2$ ligand compound was also dissolved in 50 mL of dichloromethane, and slowly added thereto. The reaction product was stirred for 3 hours, and volatiles were removed by vacuum evaporation. 100 mL of petroleum ether was added dropwise to obtain a blue solid by precipitation. The reaction product was washed twice with 100 mL of petroleum ether to obtain 1.58 g of a title compound (yield of 90%).

Synthesis Example 2

Synthesis of bis-[(phenyl)$_2$PN(isopropyl)P(phenyl)$_2$dichloride(p-chloride)chromium]

10 ml of a dichloromethane solution in which 0.16 g (0.46 mmol) of tris(tetrahydrofuran)chromium trichloride (CrCl$_3$(THF)$_3$) was dissolved was slowly added to 10 mL of dichloromethane solution in which 0.2 g (0.46 mmol) of (phenyl)$_2$ PN(isopropyl)P(phenyl)$_2$ was dissolved. The reaction mixture was stirred for 3 hours, and volatiles were removed by vacuum. 10 mL of petroleum ether was added dropwise to obtain a blue solid by precipitation. The reaction product was washed twice with 10 mL of petroleum ether to obtain 0.25 g of a title compound (yield of 98%).

Example 1

1 L of methylcyclohexane (MCH) was fed into a 2 L volumetric semi-batch reactor which was thoroughly dried and replaced with nitrogen, and 1.57 g (4 mmol) of 18 wt % mMAO-3A heptane solution and 2.0 mL (4 mmol) of 2.0 M of trimethylaluminum heptane solution were subsequently added, and a temperature of the semi-batch reactor was heated to 60° C. 3.1 mg (5.3 μmol-Cr) of bis-[(S,S)-(phenyl)$_2$PCH(methyl)CH(methyl)P(phenyl)$_2$dichloride(μ-chloride)chromium was added, and then, ethylene was filled into the reactor up to a pressure of 20 bar, and fed continuously to perform an oligomerization reaction for 2 hours. Then, ethanol containing 100 ml of 10 vol % aqueous hydrochloric acid solution was added into the reaction solution to terminate the reaction, and the reaction product was filtered and separated. The recovered reaction product was dried in a vacuum oven at 60° C. for 8 hours.

As a result, 401 g of the reaction product (LAO, C6+C8) was obtained, wherein a content of 1-hexene was 179 g and a content of 1-octene was 222 g, and polyethylene (PE) obtained as a by-product had a content of 0.04 wt % (see Table 1 below).

Example 2

A reaction product was obtained in the same manner as in Example 1, except that 0.793 g (4 mmol) of triisobutylaluminum was used instead of trimethylaluminum.

As a result, 400 g of the reaction product (LAO, C6+C8) was obtained, wherein a content of 1-hexene was 189 g and a content of 1-octene was 211 g, and polyethylene (PE) obtained as a by-product had a content of 0.53 wt % (see Table 1 below).

Example 3

A reaction product was obtained in the same manner as in Example 1, except that 1.0 ml (2 mmol) of trimethylaluminum and 0.397 g (2 mmol) of triisobutylaluminum were used instead of 2.0 ml (4 mmol) of trimethylaluminum.

As a result, 379 g of the reaction product (LAO, C6+C8) was obtained, wherein a content of 1-hexene was 173 g and a content of 1-octene was 206 g, and polyethylene (PE) obtained as a by-product had a content of 0.25 wt % (see Table 1 below).

Example 4

A reaction product was obtained in the same manner as in Example 1, except that 2.32 g (4 mmol) of 10 wt % MAO toluene solution was used instead of mMAO-3A, and 0.995 g (0.1 mmol) of 30 wt % tetraisobutylaluminoxane (TIBAO) cyclohexane solution was used instead of trimethylaluminum.

As a result, 395 g of the reaction product (LAO, C6+C8) was obtained, wherein a content of 1-hexene was 178 g and a content of 1-octene was 217 g, and polyethylene (PE) obtained as a by-product had a content of 0.80 wt % (see Table 1 below).

Example 5

A reaction product was obtained in the same manner as in Example 4, except that 3.98 g (0.4 mmol) of 30 wt % tetraisobutylaluminoxane cyclohexane solution was used.

As a result, 398 g of the reaction product (LAO, C6+C8) was obtained, wherein a content of 1-hexene was 184 g and a content of 1-octene was 214 g, and polyethylene (PE) obtained as a by-product had a content of 0.52 wt % (see Table 1 below).

Example 6

A reaction product was obtained in the same manner as in Example 4, except that 7.96 g (0.8 mmol) of 30 wt % tetraisobutylaluminoxane cyclohexane solution was used.

As a result, 368 g of the reaction product (LAO, C6+C8) was obtained, wherein a content of 1-hexene was 165 g and a content of 1-octene was 203 g, and polyethylene (PE) obtained as a by-product had a content of 0.43 wt % (see Table 1 below).

Example 7

Example 7 was performed in the same manner as in Example 4, except that ethylene and hydrogen were filled in the reactor at a pressure ratio of 19:1, and then, ethylene was continuously fed at a constant pressure of 19 bar, and hydrogen was continuously fed at a constant pressure of 1 bar, thereby performing an oligomerization reaction for 2 hours.

As a result, 427 g of the reaction product (LAO, C6+C8) was obtained, wherein a content of 1-hexene was 201 g and a content of 1-octene was 226 g, and polyethylene (PE) obtained as a by-product had a content of 0.21 wt % (see Table 1 below).

Example 8

Example 8 was performed in the same manner as in Example 5, except that ethylene (g) and hydrogen (g) were filled in the reactor at a pressure ratio of 19:1, and then, ethylene was continuously supplied at a constant pressure of 19 bar, and hydrogen was continuously fed at a constant pressure of 1 bar, thereby performing an oligomerization reaction for 2 hours.

As a result, 440 g of the reaction product (LAO, C6+C8) was obtained, wherein a content of 1-hexene was 214 g and a content of 1-octene was 226 g, and polyethylene (PE) obtained as a by-product had a content of 0.20 wt % (see Table 1 below).

Example 9

Example 9 was performed in the same manner as in Example 6, except that ethylene (g) and hydrogen (g) were filled in the reactor at a pressure ratio of 19:1, and then, ethylene was continuously fed at a constant pressure of 19 bar, and hydrogen was continuously fed at a constant pressure of 1 bar, thereby performing an oligomerization reaction for 2 hours.

As a result, 466 g of the reaction product (LAO, C6+C8) was obtained, wherein a content of 1-hexene was 223 g and a content of 1-octene was 223 g, and polyethylene (PE) obtained as a by-product had a content of 0.10 wt % (see Table 1 below).

Example 10

A reaction product was obtained in the same manner as in Example 1, except that 2.32 g (4 mmol) of 10 wt % MAO toluene solution was used in stead of mMAO-3A.

As a result, 505 g of the reaction product (LAO, C6+C8) was obtained, wherein a content of 1-hexene was 191 g and a content of 1-octene was 314 g, and polyethylene (PE) obtained as a by-product had a content of 0.047 wt % (see Table 1 below).

Example 11

A reaction product was obtained in the same manner as in Example 10 except that the used amount of trimethylaluminum in Example 10 was changed as shown in Table 1 below.

As a result, 523 g of the reaction product (LAO, C6+C8) was obtained, wherein a content of 1-hexene was 195 g and a content of 1-octene was 328 g, and polyethylene (PE) obtained as a by-product had a content of 0.17 wt % (see Table 1 below).

Example 12

A reaction product was obtained in the same manner as in Example 10 except that the used amount of trimethylaluminum in Example 10 was changed as shown in Table 1 below.

As a result, 515 g of the reaction product (LAO, C6+C8) was obtained, wherein a content of 1-hexene was 197 g and a content of 1-octene was 318 g, and polyethylene (PE) obtained as a by-product had a content of 0.1 wt % (see Table 1 below).

Example 13

A reaction product was obtained in the same manner as in Example 10 except that the used amount of trimethylaluminum in Example 10 was changed as shown in Table 1 below.

As a result, 494 g of the reaction product (LAO, C6+C8) was obtained, wherein a content of 1-hexene was 190 g and a content of 1-octene was 304 g, and polyethylene (PE) obtained as a by-product had a content of 0.16 wt % (see Table 1 below).

Example 14

A reaction product was obtained in the same manner as in Example 10 except that 0.46 g (4 mmol) of triethylaluminum was used instead of trimethylaluminum.

As a result, 144 g of the reaction product (LAO, C6+C8) was obtained, wherein a content of 1-hexene was 42 g and a content of 1-octene was 102 g, and polyethylene (PE) obtained as a by-product had a content of 0.2 wt % (see Table 1 below).

Example 15

A reaction product was obtained in the same manner as in Example 14 except that the used amount of triethylaluminum in Example 14 was changed as shown in Table 1 below.

As a result, 206 g of the reaction product (LAO, C6+C8) was obtained, wherein a content of 1-hexene was 62 g and a content of 1-octene was 144 g, and polyethylene (PE) obtained as a by-product had a content of 0.1 wt % (see Table 1 below).

Example 16

A reaction product was obtained in the same manner as in Example 14 except that the used amount of triethylaluminum in Example 14 was changed as shown in Table 1 below.

As a result, 218 g of the reaction product (LAO, C6+C8) was obtained, wherein a content of 1-hexene was 65 g and a content of 1-octene was 153 g, and polyethylene (PE) obtained as a by-product had a content of 0.14 wt % (see Table 1 below).

Example 17

A reaction product was obtained in the same manner as Example 1, except that 3.0 mg (5.3 µmol-Cr) bis-[(phenyl)$_2$PN(isopropyl)P(phenyl)$_2$ dichloride(µ-chloride) chromium] was used instead of 3.1 mg (5.3 µmol-Cr)

bis-[(S,S)-(phenyl)$_2$PCH(methyl)CH(methyl)P(phenyl)$_2$dichloride(μ-chloride)chromium].

As a result, 162 g of the reaction product (LAO, C6+C8) was obtained, wherein a content of 1-hexene was 37 g and a content of 1-octene was 125 g, and polyethylene (PE) obtained as a by-product had a content of 1.1 wt % (see Table 1 below).

Example 18

Ethylene was filled up to a pressure of 20 bar in the reactor, 1 L of methylcyclohexane (MCH) was fed into a 2 L volumetric semi-batch reactor, and 1.9 mg (5.3 μmol) of chromium (III) acetylacetonate (Cr(acac)$_3$) and 2.3 mg (5.3 mmol) of (S,S)-(phenyl)$_2$PCH(methyl)CH(methyl)P(phenyl)$_2$ ligand compound were added. Then, 1.57 g (4 mmol) of 18 wt % mMAO-3A heptane solution and 2.0 ml (4 mmol) of 2.0 M trimethylaluminum heptane solution were subsequently added thereto. Next, a temperature of the semi-batch reactor was heated to 60° C. and ethylene was continuously fed to perform the oligomerization reaction for 2 hours. Then, ethanol containing 100 ml of 10 vol % aqueous hydrochloric acid solution was added into the reaction solution to terminate the reaction, and the reaction product was filtered and separated. The recovered reaction product was dried in a vacuum oven at 60° C. for 8 hours.

As a result, it was found that 125 g of the reaction product (LAO, C6+C8) was obtained, wherein a content of 1-hexene was 40 g and a content of 1-octene was 85 g, and polyethylene (PE) obtained as a by-product had a production amount of 1 wt % or less even though it did not reach the level of Example 1.

Comparative Example 1

A reaction product (LAO, C6+C8) was obtained in the same manner as in Example 1, except that 3.14 g (8 mmol) of 18 wt % mMAO-3A heptane solution was used without using 2.0 M trimethylaluminum heptane solution.

As a result, 384 g of the reaction product (LAO, C6+C8) was obtained, wherein a content of 1-hexene was 186 g and a content of 1-octene was 198 g, and polyethylene (PE) obtained as a by-product had a content of 2.41 wt % (see Table 1 below).

Comparative Example 2

The reaction product (LAO, C6+C8) was obtained in the same manner as in Comparative Example 1 except that 4.64 g (8 mmol) of 10 wt % MAO toluene solution was used instead of mMAO-3A.

As a result, 196 g of the reaction product (LAO, C6+C8) was obtained, wherein a content of 1-hexene was 82 g and a content of 1-octene was 114 g, and polyethylene (PE) obtained as a by-product had a content of 3.44 wt % (see Table 1 below).

Comparative Example 3

A reaction product (LAO, C6+C8) was obtained in the same manner as in Comparative Example 1, except that 7.96 g (8 mmol) of 30 wt % tetraisobutylaluminoxane (TIBAO) cyclohexane solution was used instead of mMAO-3A, and a production amount thereof and an amount of by-product were measured and shown in Table 1 below.

As a result, 2 g of the reaction product (LAO, C6+C8) was obtained, wherein a content of 1-hexene was 1.27 g and a content of 1-octene was 0.73 g, and polyethylene (PE) obtained as a by-product had a content of 3.75 wt % (see Table 1 below).

Comparative Example 4

Ethylene was filled up to a pressure of 20 bar in the reactor, 1 L of methylcyclohexane (MCH) was fed into a 2 L volumetric semi-batch reactor, and 1.9 mg (5.3 μmol) of chromium (III) acetylacetonate (Cr(acac)$_3$) and 2.3 mg (5.3 mmol) of (S,S)-(phenyl)$_2$PCH(methyl)CH(methyl)P(phenyl)$_2$ ligand compound were added. Then, 1.57 g (4 mmol) of 18 wt % mMAO-3A heptane solution and 2.0 ml (4 mmol) of 2.0 M trimethylaluminum heptane solution were subsequently added thereto. Next, a temperature of the semi-batch reactor was heated to 60° C. and ethylene was continuously fed to perform the oligomerization reaction for 2 hours. Then, ethanol containing 100 ml of 10 vol % aqueous hydrochloric acid solution was added into the reaction solution to terminate the reaction, and the reaction product was filtered and separated. The recovered reaction product was dried in a vacuum oven at 60° C. for 8 hours.

As a result, 92 g of the reaction product (LAO, C6+C8) was obtained, wherein a content of 1-hexene was 21 g and a content of 1-octene was 71 g, and polyethylene (PE) obtained as a by-product had a content of 2.5 wt % (see Table 1 below).

Comparative Example 5

The reaction product (LAO, C6+C8) was obtained in the same manner as in Comparative Example 1 except that 4.0 ml (8 mmol) of 2.0M trimethylaluminum heptane solution was used instead of mMAO-3A.

As a result, 196 g of the reaction product (LAO, C6+C8) was obtained, wherein a content of 1-hexene was 82 g and a content of 1-octene was 114 g, and polyethylene (PE) obtained as a by-product had a content of 2.41 wt % (see Table 1 below).

Comparative Example 6

The reaction product (LAO, C6+C8) was obtained in the same manner as in Comparative Example 1 except that 0.92 g (8 mmol) of triethylaluminum was used instead of mMAO-3A.

As a result, 196 g of the reaction product (LAO, C6+C8) was obtained, wherein a content of 1-hexene was 82 g and a content of 1-octene was 114 g, and polyethylene (PE) obtained as a by-product had a content of 2.41 wt % (see Table 1 below).

TABLE 1

| Example | cocatalyst 1 kind | cocatalyst 1 Used amount (mmol) | cocatalyst 2 kind | cocatalyst 2 Used amount (mmol) | Hydrogen pressure (bar) | LAO production amount (g, C6 + C8) | PE (wt %) |
|---|---|---|---|---|---|---|---|
| 1 | mMAO-3A | 4 | TMA | 4 | — | 401 | 0.04 |
| 2 | mMAO-3A | 4 | Al(i-Bu)$_3$ | 4 | — | 400 | 0.53 |

TABLE 1-continued

| | | | | | | | |
|---|---|---|---|---|---|---|---|
| 3 | mMAO-3A | 4 | AlMe₃ | 2 | — | 379 | 0.25 |
| | | | Al(i-Bu)₃ | 2 | | | |
| 4 | MAO | 4 | TIBAO | 0.1 | — | 395 | 0.8 |
| 5 | MAO | 4 | TIBAO | 0.4 | — | 398 | 0.52 |
| 6 | MAO | 4 | TIBAO | 0.8 | — | 368 | 0.43 |
| 7 | MAO | 4 | TIBAO | 0.1 | 1 | 427 | 0.21 |
| 8 | MAO | 4 | TIBAO | 0.4 | 1 | 440 | 0.2 |
| 9 | MAO | 4 | TIBAO | 0.8 | 1 | 466 | 0.1 |
| 10 | MAO | 4 | TMA | 4 | — | 505 | 0.047 |
| 11 | MAO | 4 | TMA | 3 | — | 523 | 0.17 |
| 12 | MAO | 4 | TMA | 2 | — | 515 | 0.1 |
| 13 | MAO | 4 | TMA | 1 | — | 494 | 0.16 |
| 14 | MAO | 4 | TEAL | 4 | — | 144 | 0.2 |
| 15 | MAO | 4 | TEAL | 1 | — | 206 | 0.1 |
| 16 | MAO | 4 | TEAL | 0.5 | — | 218 | 0.14 |
| 17 | mMAO-3A | 4 | TMA | 4 | — | 162 | 1.1 |

| | cocatalyst 1 | | cocatalyst 2 | | | LAO | |
|---|---|---|---|---|---|---|---|
| Comparative Example | kind | Used amount (mmol) | kind | Used amount (mmol) | Hydrogen pressure (bar) | production amount (g, C6 + C8) | PE (wt %) |
| 1 | mMAO-3A | 8 | — | — | — | 384 | 2.41 |
| 2 | MAO | 8 | — | — | — | 196 | 3.44 |
| 3 | TIBAO | 8 | — | — | — | 2 | 3.75 |
| 4 | mMAO-3A | 4 | TMA | 4 | — | 92 | 2.5 |

*mMAO-3A: Modified methylaluminoxane
*MAO: Methylaluminoxane
*TMA: Trimethylaluminum
*Al(i-Bu)₃: Triisobutylaluminum
*TIBAO: Tetraisobutylaluminoxane
*TEAL: Triethylaluminum As shown in Table 1, when ethylene is oligomerized using the catalyst composition for oligomerization of ethylene according to the present invention, 1-hexene and 1-octene may be highly selectively produced at a high yield under mild conditions, and a selectivity ratio (C6:C8) for each may be easily controlled by adjusting appropriate reaction conditions. Further, in the oligomerization reaction according to the present invention, the molecular weight of polyethylene produced as a by-product may be effectively reduced, and at the same time, the production amount of polyethylene may be remarkably reduced. The synergistic effect is obtained depending on the form in which the oligomerization catalyst is introduced, and the use of the cocatalyst containing at least two combinations of aluminum compounds, which is not recognized in the related art, and further, there are no related art documents describing specifically applied examples regarding this.

Although the exemplary embodiments of the present invention have been disclosed for more details as described above, those skilled in the art will appreciate that various modifications, additions and substitutions are possible, without departing from the scope and spirit of the invention as disclosed in the accompanying claims. Therefore, the future change in the exemplary embodiments of the present invention can not depart from the technology of the present invention.

The invention claimed is:

1. A method for oligomerization of ethylene, the method comprising:
   mixing an aluminoxane and an alkyl aluminum compound to prepare a cocatalyst mixture;
   introducing the cocatalyst mixture and a oligomerization catalyst including a transition metal into a reactor;
   introducing ethylene into the reactor; and
   reacting the oligomerization catalyst, the cocatalyst mixture, and the ethylene in the reactor with each other,
   wherein the oligomerization catalyst is a complex in which the transition metal and a heteroatom ligand represented by Chemical Formula 2 below are coordinated to each other

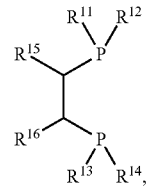

[Chemical Formula 2]

where, in Chemical Formula 2, $R^{11}$ to $R^{14}$ are each independently substituted or unsubstituted hydrocarbyl or substituted or unsubstituted heterohydrocarbyl; and
$R^{15}$ and $R^{16}$ are each independently substituted or unsubstituted hydrocarbyl, or $R^{15}$ and $R^{16}$ may be bonded to each other to form a ring.

2. The method of claim 1, wherein the aluminoxane is methylaluminoxane or modified methylaluminoxane, and
the alkyl aluminum compound is one or more selected from isobutylaluminoxane, tetraisobutylaluminoxane, trimethylaluminum, triethylaluminum, tripropylaluminum, triisobutylaluminum, diisobutylaluminum, and trioctylaluminum.

3. The method of claim 1, wherein $R^{15}$ and $R^{16}$ are bonded to each other to form an alicyclic ring or aromatic ring.

4. The method of claim 1, wherein the transition metal is chromium.

5. The method of claim 1, wherein the cocatalyst mixture is introduced into the reactor at a range from 1 to 10000 moles based on 1 mole of the oligomerization catalyst.

6. The method of claim 1, wherein the cocatalyst mixture includes the aluminoxane and the alkyl aluminum compound at a molar ratio of 1:0.01 to 1:100.

7. The method of claim 1, wherein the reacting is performed in the presence of hydrogen.

8. The method of claim 1, wherein the reacting is performed at a temperature range from 0 to 200° C.

9. The method of claim 8, wherein the reacting is performed at a temperature range from 20 to 100° C.

10. The method of claim 1, wherein the reacting is performed at a pressure range from 1 to 500 bar.

11. The method of claim 1, wherein 1-hexene, 1-octene, or a mixture thereof is selectively produced.

12. The method of claim 1, further comprising:
    mixing the cocatalyst mixture and the oligomerization catalyst before introducing the cocatalyst mixture and the oligomerization catalyst into the reactor.

13. The method of claim 1, wherein the introducing the cocatalyst mixture and the oligomerization catalyst includes:
    introducing the cocatalyst mixture into the reactor; and
    introducing the oligomerization catalyst into the reactor.

\* \* \* \* \*